United States Patent [19]

Schatz

[11] Patent Number: 5,785,715
[45] Date of Patent: Jul. 28, 1998

[54] RETRIEVAL SHUTTLE

[76] Inventor: Richard A. Schatz, P.O. Box 8517, Rancho Santa Fe, Calif. 92067

[21] Appl. No.: 569,724

[22] Filed: Dec. 7, 1995

[51] Int. Cl.⁶ ..................................................... A61F 11/00
[52] U.S. Cl. ..................................................... 606/108; 606/1
[58] Field of Search ........................... 606/1, 108, 192.2; 623/1, 11, 12

[56] References Cited

U.S. PATENT DOCUMENTS

| | | |
|---|---|---|
| 3,657,744 | 4/1972 | Ersek . |
| 3,993,078 | 11/1976 | Bergentz et al. . |
| 4,130,904 | 12/1978 | Whalen . |
| 4,313,231 | 2/1982 | Koyamada . |
| 4,315,509 | 2/1982 | Smit . |
| 4,562,596 | 1/1986 | Kornberg . |
| 4,594,996 | 6/1986 | Ibrahim et al. . |
| 4,732,152 | 3/1988 | Wallsten et al. . |
| 4,733,665 | 3/1988 | Palmaz . |
| 4,739,762 | 4/1988 | Palmaz . |
| 4,776,337 | 10/1988 | Palmaz . |
| 4,793,348 | 12/1988 | Palmaz . |
| 4,800,882 | 1/1989 | Gianturco . |
| 5,275,605 | 1/1994 | Winkler .................. 606/127 |
| 5,330,482 | 7/1994 | Gibbs et al. ............. 606/113 |
| 5,334,208 | 8/1994 | Soehendra et al. ........ 606/108 |
| 5,474,563 | 12/1995 | Myler et al. ............. 606/108 |
| 5,628,754 | 5/1997 | Shevlin et al. .......... 606/192 |
| 5,634,937 | 6/1997 | Mollenauer et al. ....... 606/192 |

FOREIGN PATENT DOCUMENTS 0 274 846 A1   7/1988   European Pat. Off. .
2 104 673      3/1972   Germany .

*Primary Examiner*—Glenn K. Dawson
*Attorney, Agent, or Firm*—Crompton, Seager & Tufte, LLC

[57] ABSTRACT

The present invention is a retrieval shuttle for removal of a stent, medical prosthesis or other foreign object from the vessel of a patient. Structurally, the present invention includes a resilient positioning catheter formed to surround a lumen. A shuttle body also formed to include a lumen is attached to the distal end of the positioning catheter. A flexible bladder formed to surround a passageway is positioned as an inner layer for the lumen of the shuttle body forming a pressurizable chamber between the shuttle body and the flexible bladder. Fluid passed through the positioning catheter pressurizes the chamber causing the flexible bladder to progressively collapse. Operationally, the present invention is advanced through the vessel of the patient to position the passageway of the flexible bladder around the stent or other object requiring removal. The chamber is then pressurized to collapse the flexible bladder around the stent, holding the stent. The retrieval shuttle, with the stent held in the passageway of the flexible bladder, is then removed from the patient.

7 Claims, 2 Drawing Sheets

RETRIEVAL SHUTTLE

RELATED CASE

The present application is related to U.S. patent application Ser. No. 08/557,723, filed Nov. 13, 1995, entitled "STENT RETRIEVAL CATHETER".

FIELD OF THE INVENTION

The present invention pertains generally to medical devices which are used in cardio-vascular surgery. More particularly, the present invention pertains to medical devices and prosthesis which are inserted into the vessel of a patient during cardio-vascular surgery or other medical procedures. The present invention is particularly, but not exclusively useful for retrieving a medical device or other object from the vessel of a patient in the event the device or object is not able to achieve beneficial results.

BACKGROUND OF THE INVENTION

The placement of medical devices, such as vascular stents, within the vascular system of a patient to give vessels added structural stability is a well known and increasingly common procedure. In fact, a large number of differing stents and other prosthesis have been developed for deployment within the vascular system for this purpose. In practice, devices of this nature are often inserted over a prepositioned guide wire and advanced into the vessel until the device reaches a predetermined deployment site. Generally, the route over which the stent or other device must be advanced is often long and quite frequently very tortuous.

Sometimes, during the deployment of a vascular stent or prosthesis, it may happen that the stent will be inadvertently positioned in an incorrect location. Alternatively, it may happen that a stent or other device will outlive its useful life. In these and other cases, it may become necessary to retrieve the stent from within the vascular system for removal from the patient. Unfortunately, the removal of a stent from the vascular system can be a difficult process. For one thing, removal generally requires dragging the stent back through the tortuous route by which the stent was originally deployed. When doing so, it may happen that the stent will catch, or snag, on various anatomical features within the vascular system. As a result, there is a danger that the removal process will actually traumatize the involved vessel.

The difficulty associated with stent removal is often compounded by the lack of medical instruments which are designed for the specific task of stent removal. More specifically, it is generally the case that removal of stents, and other medical prosthesis, will often be accomplished using makeshift instruments. For example, the snaring or snagging of a stent for removal from a vessel is often accomplished using a hooked instrument which has been improvised at the time of the actual procedure. As may be expected, however, expediently made instruments are often difficult to use and may cause additional vascular trauma if the hook is allowed to contact the vessel wall. Additionally, when these devices are employed, there is an ever present danger that the stent or prosthesis will become disconnected from the retrieval device during the retrieval process. A disconnection of this type further increases the difficulty and risk associated with the removal process.

In light of the above, it is an object of the present invention to provide a device for retrieving a stent from the vessel of a patient which can grip onto and hold the stent during its removal from the vessel. Another object of the present invention is to provide a device for retrieving a stent from the vessel of a patient which can minimize traumas to the vessel during the removal process. Yet another object of the present invention is to provide a device for retrieving a stent from the vessel of a patient which is simple to use, relatively easy to manufacture and comparatively cost effective.

SUMMARY OF THE PREFERRED EMBODIMENTS

The present invention is a retrieval shuttle for removal of a foreign object, such as a stent or other object, from the vascular system of a patient. Structurally, the present invention includes a shuttle body attached to the distal end of an elongated positioning catheter or tube. The shuttle body is formed from a substantially rigid material, such as biocompatible polymers or metals and surrounds a lumen which is dimensioned to receive the stent, medical prosthesis or foreign object requiring removal. The positioning catheter is also formed with a lumen and is preferably formed from a relatively rigid but somewhat resilient and flexible material such as polyester or hypodermic-type tubing.

The present invention also includes a flexible bladder having a proximal end and a distal end. The flexible bladder is formed to surround a passageway and is positioned inside of the lumen of the shuttle body. For a first embodiment of the present invention, the flexible bladder is positioned to be substantially coaxial with the lumen of the shuttle body. The distal end of the flexible bladder is circumferentially sealed to the distal end of the lumen of the shuttle body. Similarly, the proximal end of the flexible bladder is circumferentially sealed to the proximal end of the lumen of the shuttle body. As a result, the flexible bladder is structurally positioned as an inner layer for the lumen of the shuttle body. Thus, a pressurizable chamber is formed between the flexible bladder and the lumen of the shuttle body. Further, the lumen of the positioning catheter is connected in fluid communication with this pressurizable chamber. In the operation of the present invention, fluid supplied under pressure through the lumen of the positioning catheter pressurizes the chamber that is formed between the lumen of the shuttle body and the flexible bladder. This pressurization applies a force to the flexible bladder which expands the flexible bladder in a manner which causes the passageway of the flexible bladder to progressively collapse.

To remove a stent or prosthesis from a body vessel, the positioning catheter is manipulated to progressively advance the shuttle body through the vessel of the patient over a guidewire or stent delivery balloon shaft. Once the stent or prosthesis requiring removal is reached, the shuttle body is advanced to position the stent inside the lumen of the shuttle body and inside of the passageway of the flexible bladder. Fluid is then passed through the lumen of the positioning catheter to pressurize the chamber that is formed between the lumen of the shuttle body and the flexible bladder. As mentioned above, the pressurization causes the passageway of the flexible bladder to progressively collapse to surround and hold the stent. With the flexible bladder collapsed to hold the stent, the positioning catheter is manipulated to withdraw the shuttle body and the stent from the patient, completing the procedure.

For an alternate embodiment of the present invention, a flexible bladder is positioned within the lumen of the shuttle body. The distal end of the flexible bladder is closed and the proximal end of the flexible bladder is connected in fluid communication with the lumen of the positioning catheter. Importantly, the flexible bladder is attached to the shuttle body to hold the flexible bladder in the lumen of the shuttle body. Fluid can then be supplied under pressure to cause the flexible bladder to selectively expand in the lumen of the shuttle body. Operationally, the positioning catheter is manipulated to progressively advance the shuttle body through the vessel of the patient. Once the stent or prosthesis requiring removal is reached, the shuttle body is advanced to position the stent inside the lumen of the shuttle body and next to the flexible bladder. Fluid is then passed through the lumen of the positioning catheter to expand the flexible bladder. The expanding flexible bladder thus traps the stent between the flexible bladder and the lumen of the shuttle body to hold the stent within the lumen of the shuttle body. With the flexible bladder expanded to hold the stent, the positioning catheter is manipulated to withdraw the shuttle body and the stent from the patient, completing the procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
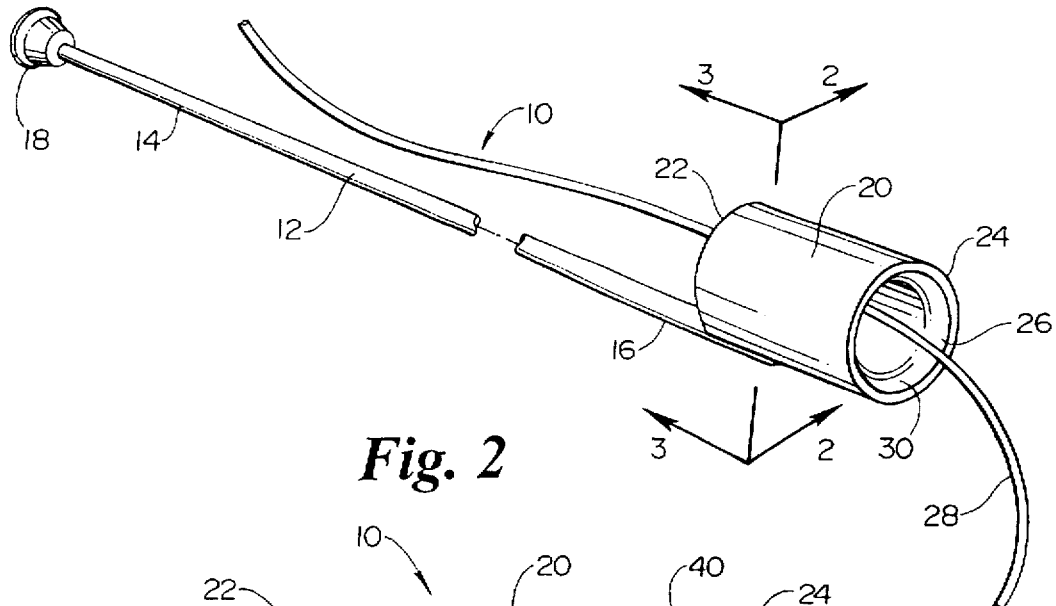
FIG. 1 is a perspective view of the retrieval shuttle of the present invention.

Referring initially to FIG. 1, the retrieval shuttle of the present invention is shown and generally designated 10. In general terms, it may be seen that the retrieval shuttle 10 includes a positioning catheter 12 having a proximal end 14 and a distal end 16. A connector 18 is attached to the proximal end 14 of the positioning catheter 12. Preferably, the positioning catheter 12 is formed from a relatively rigid but somewhat resilient and flexible material such as polyester or hypodermic-type tubing.

The present invention also includes a shuttle body 20. The shuttle body 20 is formed from a substantially rigid material, such as polyester or metal and is attached to the distal end 16 of the positioning catheter 12. The shuttle body 20 has a proximal end 22 and a distal end 24. Additionally, the shuttle body is formed to surround a lumen 26 which passes between the distal end 24 and the proximal end 22 of the shuttle body 20. FIG. 1 also shows that the present invention is intended to be usable in combination with a guide wire 28.

Figure 2:
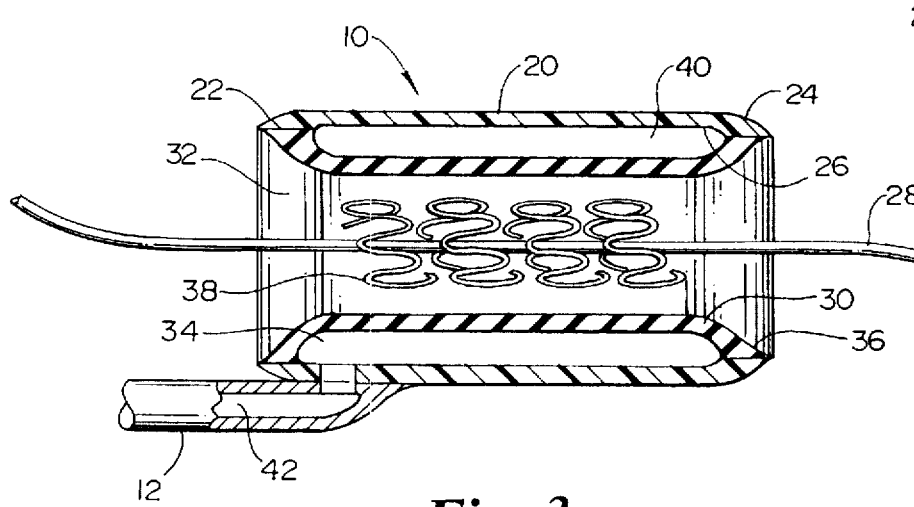
FIG. 2 is a cross-sectional view of the shuttle body of the present invention taken along the lines marked 2—2 in FIG. 1.
Figure 3:
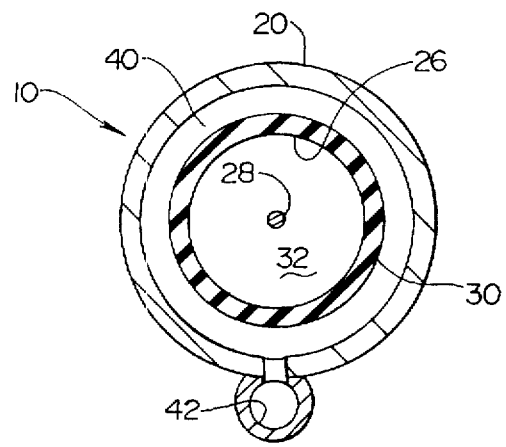
FIG. 3 is a cross-sectional view of the shuttle body of the present invention taken along the lines marked 3—3 in FIG. 1.

The structural details of the present invention are more easily appreciated by reference to FIGS. 2 and 3. In FIGS. 2 and 3, it may be seen that the a flexible bladder 30 is positioned inside of the lumen 26 of the shuttle body 20. The flexible bladder 30 is formed to surround a passageway 32 and has a proximal end 34 and a distal end 36. The proximal end 34 of the flexible bladder 30 is circumferentially sealed to the proximal end 22 of the shuttle body 20. Similarly, the distal end 36 of the flexible bladder 30 is circumferentially sealed to the distal end 24 of the shuttle body 20. Also, the passageway 32 of the flexible bladder 30 is dimensioned so that stent 38 may be received into the passageway 32 of the flexible bladder 30. In FIG. 3, it is seen that the flexible bladder 30 is positioned coaxially with respect to shuttle body 20 and that placement catheter 12 is in fluid communication with chamber 40 that is established between flexible bladder 30 and shuttle body 20. It is to be appreciated that the present invention is intended to be usable for the retrieval of a wide range of stents, like stent 38, as well as a wide range of medical prosthesis and other foreign objects. It is also to be appreciated that the present invention is specifically intended to be usable in vessels of varying size. As a result, the present invention specifically envisions that retrieval shuttle 10, and passageway 32 may be fabricated over a range of useful dimensions.

Figure 4:
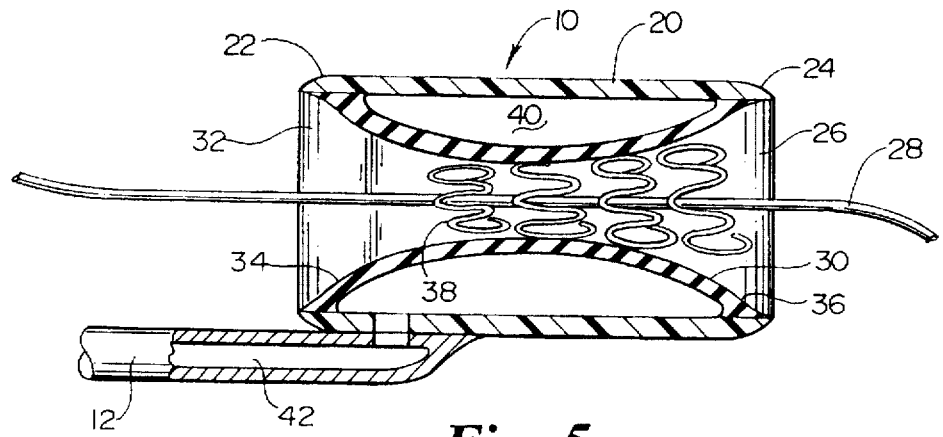
FIG. 4 is a cross-sectional view of the shuttle body of the present invention as shown in FIG. 2, with the flexible bladder now shown in a collapsed configuration.

Turning now to FIG. 4, it may be seen that a pressurizable chamber 40 is formed between the shuttle body 20 and the flexible bladder 30. Additionally, it may be seen in both FIGS. 3 and 4 that the positioning catheter 12 is formed with a lumen 42 and that the lumen 42 of the positioning catheter 12 is attached in fluid communication with the pressurizable chamber 40. Functionally, a source of fluid pressure (not shown) is attached to the connector 18 at the distal end of the positioning catheter 12. The fluid travels through the lumen 42 of the positioning catheter 12 to pressurize the chamber 40. Pressurization of the chamber 40 applies pressure to the flexible bladder 30 causing the flexible bladder 30, and the passageway 32 of the flexible bladder 30 to progressively collapse.

The ability of the flexible bladder 30 to progressively collapse may be better appreciated by comparison of FIG. 2 and FIG. 4. More specifically, it may be seen in FIG. 2 that the flexible bladder 30 is substantially uncollapsed. By comparison, in FIG. 4, the passageway 32 of the flexible bladder 30 has distended radially inward, partially collapsing flexible bladder 30. Importantly, it may be seen in FIG. 2 that the stent 38 is physically smaller than the passageway 32 of the flexible bladder 30. As a result, the stent 38 is free to move within the flexible bladder 30. In contrast, in FIG. 4, the passageway 32 of the flexible bladder 30 has partially collapsed around the stent 38. As a result, the stent 38 is held in the flexible bladder 30.

Figure 5:
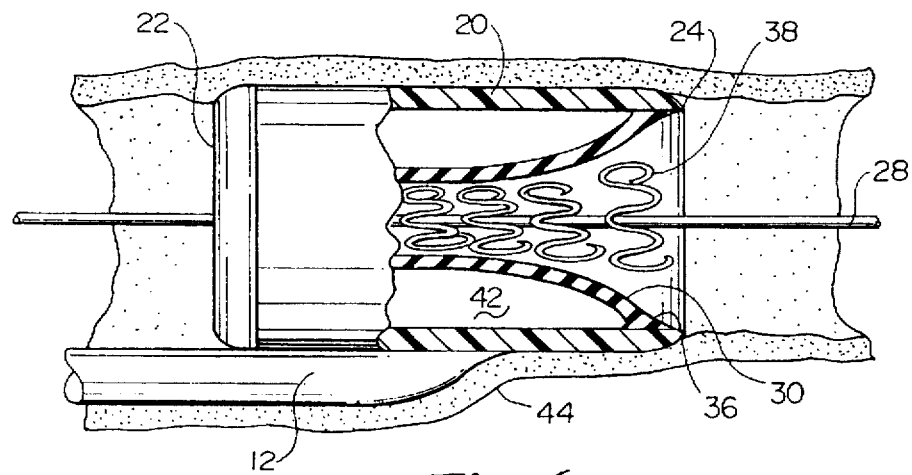
FIG. 5 is a partial cut-away of the retrieval shuttle of the present invention shown operationally positioned in the vessel of a patient.

Operation of the present invention, as best seen in FIG. 5, begins with insertion of the distal end 16 of the positioning catheter 12 and shuttle body 20 into the vessel of a patient. The positioning catheter 12 is then manipulated to progressively advance the shuttle body 20 through the vessel, until the shuttle body 20 is adjacent to the stent 38 or other removal target. In many cases, advancement of the shuttle body 20 will be facilitated by use of a prepositioned guide wire, such as the guide wire 28. In cases of this type, the guide wire 28 is inserted through the lumen 26 of the shuttle body 20 and the shuttle body 20 is advanced over the guide wire 28 until the target to be removed has been reached.

Once the shuttle body 20 has reached the stent 38, the positioning catheter is further manipulated to advance the shuttle body 20 over the stent 38 until stent 38 is partially or fully contained in the lumen 26 of the shuttle body 20. This may be more fully appreciated by reference to FIG. 3 where it may be seen that the shuttle body 20 and distal end 16 of the positioning catheter 12 have been advanced through a vessel 44 to position the stent 38 partially inside of the lumen 26 of the shuttle body 20.

Fluid is then passed through the lumen 42 of the positioning catheter 12, pressurizing the chamber 40 that is formed between the lumen 26 of the shuttle body 20 and the flexible bladder 30. The pressurization causes the passageway 32 of the flexible bladder 30 to progressively collapse, or deform, to surround and hold the stent 38. The deformation of the flexible bladder 30 is clearly shown in FIG. 5, where it may be seen that the flexible bladder 30 has collapsed to surround the stent 38. With the flexible bladder 30 collapsed to hold the stent 38, the positioning catheter 12 is manipulated to withdraw the shuttle body 20 and the stent 38 from the patient, completing the procedure.

Figure 6:
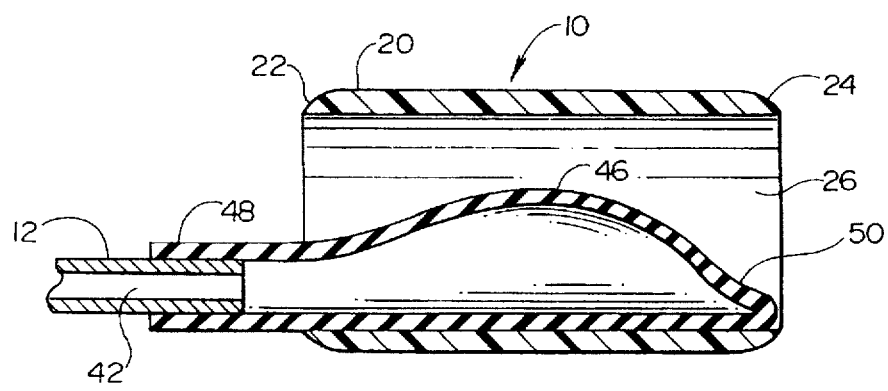
FIG. 6 is a cross-sectional view of an alternate embodiment for the shuttle body of the present invention.

Turning now to FIG. 6, an alternative embodiment of the retrieval shuttle is shown and generally designated 10'. As shown in FIG. 6, retrieval shuttle 10' includes the same positioning catheter 12 and shuttle body 20 as retrieval shuttle 10 of FIG. 2. For retrieval shuttle 10', however, flexible bladder 30 of FIG. 2 has been replaced by flexible bladder 46. More specifically, it may be seen that flexible bladder 46 has a proximal end 48 and a distal end 50. Unlike flexible bladder 24, however, the distal end 50 of flexible bladder 46 is sealed. Additionally, the proximal end 48 of flexible bladder 46 is connected in fluid communication to the lumen 42 of the positioning catheter 12. Functionally, fluid passes from the fluid pressure source (not shown) through the positioning catheter 12 and into the flexible bladder 46. The passage of fluid into the flexible bladder 46 causes the flexible bladder 46 to expand to selectively occupy the lumen 26 of the shuttle body 20.

Operation of the retrieval shuttle 10' generally follows the same sequence of steps utilized in the case of retrieval shuttle 10. In the case of retrieval shuttle 10' however, the removal target is received into the lumen 26 of the shuttle body 20 to be adjacent to the flexible bladder 46. The flexible bladder 46 is then selectively expanded by operation of the fluid pressure source to trap the removal target between the expanded flexible bladder 46 and the lumen 26 of the shuttle body 20. The positioning catheter 12, shuttle body 20 and removal target are then removed from the patient completing the procedure.

While the particular retrieval shuttle as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A device for retrieval of a foreign object from the vessel of a patient, said device comprising:

a positioning catheter formed with a lumen, said positioning catheter having a distal end and a proximal end;

a shuttle body attached to said distal end of said positioning catheter for movement therewith, said shuttle body formed from a substantially rigid material to surround a lumen;

inflatable means positioned in said lumen of said shuttle body and attached in fluid communication with said lumen of said positioning catheter for selective inflation thereof to hold said foreign object in said lumen of said shuttle body; wherein said inflatable means comprises a flexible bladder, said flexible bladder having a proximal end and a distal end, wherein said proximal end of said flexible bladder is circumferentially sealed to said proximal end of said shuttle body and said distal end of said flexible bladder is circumferentially sealed to said distal end of said shuttle body to form a chamber between said flexible bladder and said shuttle body, said chamber pressurizable to selective expand said flexible bladder to surroundingly hold said foreign object.

2. A device as recited in claim 1 wherein said shuttle body is formed as a tube.

3. A device as recited in claim 1 wherein said lumen of said shuttle body is dimensioned to receive a vascular stent.

4. A device for retrieval of a foreign object from the vessel of a patient, said device comprising:

a substantially rigid shuttle body, said shuttle body formed to surround a lumen and having a proximal end and a distal end;

a flexible bladder formed to surround a passageway, said passageway dimensioned to receive said foreign object, said flexible bladder having a proximal end and a distal end, said flexible bladder positioned inside said lumen of said shuttle body, said proximal end of said flexible bladder circumferentially sealed to said proximal end of said shuttle body, said distal end of said flexible bladder circumferentially sealed to said distal end of said shuttle body to form a chamber between said flexible bladder and said shuttle body, said chamber pressurizable to selectively collapse said flexible bladder to surroundingly hold said foreign object; and a flexible positioning catheter, said positioning catheter attached to said shuttle body, said positioning catheter formed with a lumen, said lumen attached in fluid communication with said chamber.

5. A device as recited in claim 4 further comprising a fluid pressure source, said fluid pressure source connected to said lumen of said positioning catheter, said fluid pressure source controllable to pressurize said chamber to selectively collapse said flexible bladder.

6. A device has recited in claim 4 wherein said passageway is dimensioned to receive a vascular stent.

7. A method for retrieving a stent from the vessel of a patient, said method comprising the steps of:

providing a device which comprises a positioning catheter formed with a lumen, said positioning catheter having a distal end and a proximal end, a shuttle body attached to said distal end of said positioning catheter for movement therewith, said shuttle body formed to surround a lumen;

inflatable means positioned in said lumen of said shuttle body and attached in fluid communication with said lumen of said positioning catheter for selective inflation thereof to hold said stent in said lumen of said shuttle body;

advancing said device in said vessel to reach said stent;

further advancing said device to position said stent in said lumen of said shuttle body;

selectively inflating said inflatable means to hold said stent; and withdrawing said device and said stent from said vessel.

* * * * *